United States Patent
Callac et al.

(10) Patent No.: US 6,521,817 B2
(45) Date of Patent: Feb. 18, 2003

(54) HYBRID STRAINS OF *AGARICUS BISPORUS*, GERMINATION OF THE SPORES OF WHICH PROVIDES MAINLY HOMOKARYONS, PRODUCTION AND USE THEREOF

(75) Inventors: Philippe Callac, Villenave d'Ornon (FR); Micheline Imbernon, Talence (FR); Christophe Billette, Castres (FR)

(73) Assignees: C.T.C. Centre Technique du Champignon et Institut, St. Paterne Racan (FR); National de la Recherche Agronomique, Paris (FR)

( * ) Notice: Subject to any disclaimer, the term of this patent is extended or adjusted under 35 U.S.C. 154(b) by 0 days.

(21) Appl. No.: 09/002,953

(22) Filed: Jan. 5, 1998

(65) Prior Publication Data

US 2002/0059655 A1 May 16, 2002

Related U.S. Application Data

(63) Continuation of application No. 08/403,750, filed as application No. PCT/FR93/00947 on Sep. 28, 1993, now abandoned.

(30) Foreign Application Priority Data

Sep. 28, 1992 (FR) .............................. 92 11536

(51) Int. Cl.$^7$ ........................ A01H 15/00; A01H 11/00; A01G 1/04
(52) U.S. Cl. ......................... 800/297; 800/295; 47/1.1
(58) Field of Search .............................. 800/297, 295; 47/1.1

(56) References Cited

U.S. PATENT DOCUMENTS

| 4,996,390 A | | 2/1991 | Dahlberg | |
| 5,304,721 A | * | 4/1994 | Kerrigan et al. | 800/200 |
| 5,563,317 A | * | 10/1996 | Kerrigan et al. | 800/200 |

FOREIGN PATENT DOCUMENTS

| DE | 3428988 | 12/1984 |

OTHER PUBLICATIONS

Strategies for the efficient recovery of *Agaricus bisporus* homokaryons. kerrigan et al. Mycologia 84 (4) 575–579 1992.*
Genes II Benjamin Lewin. 1985.*
Castle et al. Applied and Environmental Microbiology, vol. 54, NO. 7, Jul. 1988, 1643–1648.*
P. Callac et al., "The Two Life Cycles of Agaricus Bisporus", *Mushroom Biology and Mushroom Products*, p. 57–66, (1996).

M. Imbernon et al., Allelic Polymorphism at the Mating Type Locus in Agaricus Bisporus var. Burnetti, and Confirmation of the Dominance of its Tetrasporic Trait, *Science and Cultivation of Edible Fungi*, pp. 11–19, (1995).
Philippe Callac, "Morphological, Genetic, and Interfertility Analyses Reveal a Novel, Tetrasporic Variety of Agaricus Bisporus from the Sonoran Desert of California", *Mycologia*, vol. 85, No. 5, pp. 835–851, (1993).
R. Kerrigan et al., "The Heterothallic Life Cycle of Agaricus Bisporus var. Burnettii and the Inheritance of its Tetrasporic Trait", *Experimental Mycology*, vol. 18, pp. 193–210, (1994).
P. Callac, "Breeding of Edible Fungi with Emphasis on the Variability Among French Genetic Resources of Agaricus Bisporus", *Can. J. Bot.*, vol. 73(Suppl. 1), pp. S980–S986, (1995).
G. Fritsche et al., "The Cultivation of Mushrooms", *Mushroom Strains*, pp. 101–123, (1988).
P. Horgen et al., "The Use of Protoplast Production, Protoplast Regeneration and Restriction Fragment Length Polymorphisms in Developing a Systematic and High Reproduceable Breeding Strategy for Agaricus Bisporous", *Genetics and Breeding of Agaricus*, pp. 62–72, 1991.
S. Song et al., "Observations on the Spored–Basidium in the Cultivated Mushroom (Agaricus Bisporus)", *Mushroom Science*, vol. 8, pp. 295–303, (1972).
R. Dickhardt, "Homokaryotization of Agaricus Bitorquis (Quel.) Sacc. And Agaricus Bisporus (Lange) Imb.", *Theoretical Applied Genetics*, vol. 70, pp. 52–56, (1985).
A. Castle et al., "Crosses Among Homokaryons from Commercial and Wild–Collected Strains of the Mushroom Agaricus Brunnescens (=A. Bisporus)", *Applied and Environmental Microbiology*, vol. 54, No. 7, Jul. 1988, pp. 1643–1648.
J. Pelham, "Techniques for Mushroom Genetics," *Mushroom Sc ience*, vol. 5, No. 30–32, pp. 49–64, (1965).

* cited by examiner

Primary Examiner—Bruce R. Campbell
Assistant Examiner—Annette H. Para
(74) Attorney, Agent, or Firm—Oliff & Berridge, PLC

(57) ABSTRACT

"Novel hybrid strains of *Agaricus bisporus*, the germination of the spores of which provides mostly homocaryons, their production and their use".

Hybrid strain of Agaricus having the following traits:
  it is interfertile with *Agaricus bisporus*,
  its fructifications have basidia of which less than 15% are bisporous,
  and most of the spores on said fructifications are homocaryotic,
and whose traits can be genetically transmitted; method of obtaining such a strain, and its use for obtaining modified strains of *Agaricus bisporus*.

4 Claims, No Drawings

HYBRID STRAINS OF AGARICUS BISPORUS, GERMINATION OF THE SPORES OF WHICH PROVIDES MAINLY HOMOKARYONS, PRODUCTION AND USE THEREOF

This is a Continuation of application Ser. No. 08/403,750, filed Apr. 26, 1995 (U.S. National Stage of PCT/FR93/00947 filed Sep. 28, 1993) now abandoned. The entire disclosure of the prior application is hereby incorporated by reference herein in its entirety.

The present invention relates to novel hybrid strains of *Agaricus bisporus* whose fructifications have a mostly tetrasporous and/or trisporous nature under standard culture conditions and allow homocaryons to be obtained in large amounts.

The invention also relates to a process for the production of such hybrid strains and/or to the use of these hybrid strains in a process for obtaining and selecting improved strains of *Agaricus bisporus*.

Furthermore, the invention relates to the use of such hybrids which have mostly tetrasporous and/or trisporous fructifications for obtaining considerable amounts of homocaryons and/or in a process for obtaining a bisporus Agaricus strain which has been improved by carrying out a cross (crosses) and by selection.

If the present application uses the term "strain" without being more specific, this is to be understood as meaning a strain of *Agaricus bisporus* or a strain which is interfertile with *Agaricus bisporus*. Moreover, the term "tetrasporous", without being more specific, can denote, for example, "mostly tetrasporous and/or trisporous, and to a minor extent bisporous", in particular when it is clear that the intended aim is to be able to have a large number of homocaryons available. The term "having mostly tetrasporous basidian" can, for analogous reasons, also denote "whose spores are mostly homocaryotic". The term "homocaryotic spore" here indicates spores whose germination provides homocaryotic mycelia (or homocaryons).

It is known that the species of the genus Agaricus have basidia which are usually tetrasporous. The cultivated mushroom is a notable exception, having mostly bisporous basidia (generally in an amount of at least 90%). From this results the name of this species: *Agaricus bisporus*.

The spores of *Agaricus bisporus* normally contain two non-fraternal nuclei generated by meiosis, and their germination into a monosporous culture gives fruiting heterocaryotic mycelia, that is to say they are capable of fruit formation without confrontation with a compatible mycelium.

*Agaricus bisporus* is therefore a secondary homothallic bisporous species, according to the definition of J. R. RAPER, "Genetics of Sexuality in Higher Fungi", The Remaid Press Cy, New York, 1966. Its sexual type is bipolar, which can be expressed by the fact that each of the mycelia from one of the four spores of one of the rare tetrasporous basidia is compatible with two of the mycelia from the other three spores.

In view of its homothallic nature, it is difficult to obtain large amounts of homocaryons of *Agaricus bisporus*, which would be necessary for carrying out selection strategies by crossing.

This is partly why the genetic variability between the strains which are traditionally grown is, in fact, restricted to six classes of genotypes, two of these classes having the characteristic white which originates from mutants which appeared during the cultivation, one in 1926 and the other in 1960. A seventh class termed "hybrid class" results from a cross which was carried out between the two white strains.

Moreover, there are wild-type strains of *Agaricus bisporus*, but these strains have a dominant brown characteristic which makes it difficult for them to be used in the generation of hybrids.

In connection with everything that has been said in this matter, for example, G. Fritsche and A. S. M. Sonnenberg, "The cultivation of Mushrooms" Van Griensven Ed. (1988), pages 101–123, can be cited.

The existing methods for obtaining homocaryons of *Agaricus bisporus* are difficult to carry out and, above all, only give rise to small amounts of different homocaryons. These methods consist either in germinating the spores and isolating and identifying mycelia from spores of the rare tetrasporous basidia, or in isolating the spores from tetrasporous basidia by means of micro-manipulation, or else in isolating protoplasts by means of enzymatic lysis of the wall of multinucleate heterocaryotic cells, which constitute the mycelium; see, for example, G. Fritsche and A. S. M. Sonnenberg, the paper cited above.

It is known that a range of methods can be used to identify homocaryotic mycelia and to distinguish them from heterocaryotic mycelia, for example:

observation of the mycelial growth, which is generally less vigorous in the case of the homocaryotic mycelia;

experiments in which the homocaryotic mycelia are confronted with homocaryons having different incompatibility alleles;

experiments on the formation of fruiting bodies;

the use of one or, preferably, more biochemical markers, in particular enzymatic markers, especially alloenzymes (May and Royse, Experimental Mycology, Vol. 6, pages 283–292, 1982;

or else the use of one or more molecular markers (for example RFLP or RAPD markers); see, for example, "Genetics and Breeding of Agaricus", Proceedings of the First International Seminar on Mushroom Science, Horst (Netherlands), May 14–17, 1991, L. J. L. D. Van Griensven Ed, PUDOC Wageningen 1991, in particular pages 62–72 (P. A. Horgen et al.) and pages 73–77 (R. S. Khush et al.).

The biochemical and molecular markers can be used in two ways: either it is known that the mother strain is heterozygous, and for example the loss of heterozygosis in the test mycelium shows that it must be homocaryotic, or else a mycelium M which is presumed to be homocaryotic is confronted with an intercompatible homocaryon carrying an allele which differs from the marker being studied, and if the resulting mycelium is heteroallelic, the mycelium M was indeed homocaryotic, and in this latter case the use of a single marker suffices to draw conclusions.

It has now been found that there are wild-type strains of Agaricus which are bisporous to a very minor extent, of which for example at least 80% of the basidia have more than two spores (in particular four spores), which are interfertile with the wild-type strains and the commercial strains of *Agaricus bisporus*, and whose hybrids with *Agaricus bisporus* are mostly tetrasporous and/or trisporous without any particular measures to this end being taken. In other words, this trait of being tetrasporous and to a minor extent bisporous is dominant in such a hybridization. Moreover, said hybrids themselves are interfertile with *Agaricus bisporus*.

Such wild-type strains can be found in particular in California in the Sonoran desert. One of these strains is supplied under the no. ARP 61 by the Agaricus Recovery Program (abbreviated: ARP) Post Office Box 461, Worthington Pa. 16262, USA.

Other analogous strains which are bisporous to a minor extent, such as ARP 15 (also termed "JB2" and deposited at the ATCC under the no. 76072) and possibly certain strains selected from amongst strains ARP 116 to 167 can also be obtained from the ARP.

Because of the fact that the tetrasporous phenotype of these wild-type strains can surprisingly be dominantly transmitted to hybridization products, it is possible to use those wild-type strains whose fructifications have mostly homocaryotic spores to carry out crosses with strains of *Agaricus bisporus* which give rise to hybrids whose tetrasporous and/or trisporous nature (the majority of the spores thus being homocaryotic) allows homocaryons to be obtained for the first time in considerable quantities, of which it is known that they are required for carrying out subsequent hybridization crosses with a view to obtaining improved hybrid varieties by selection.

It must be remembered that the rare known cases of strains in which a sizeable number of basidia have more than two spores were the result of specific culture conditions (environment) and not of a trait which can be transmitted genetically; see, for example, J. Pelham, Mushroom Science 7, pages 49–64 (1965) and S. F. Song et al., Mushroom Science 8, 295–303 (1972). It should be noted here that in the tetrasporous strains used and/or obtained according to the present invention, the tetrasporous nature can be transmitted and is observed under standard culture conditions, which can be, for example, the following: compost on the basis of horse manure and straw; stage in which the compost is colonized by the mycelium: 24–25° C.; casing material: mixture of calcareous tufa and peat; temperature after applying the casing material: 15–18° C.; relative humidity 85–95%.

The invention thus allows traditional selection plans to be developed which could previously only be applied to strains of heterothallic fungi. Methods of controlled interfertilization are made considerably easier, and methods of free interfertilization are made possible. Methods of subjecting spores of tetrasporous strains to mutagenesis and, possibly, methods of selection between homocaryotic fructifications can also be considered.

Some examples which allow the significance of the invention to be better understood are given hereinbelow.

Let X be a bisporous strain of *Agaricus bisporus*. A homocaryon can be isolated by traditional methods which have been mentioned hereinabove. This homocaryon of X is confronted with a compatible homocaryon from a tetrasporous interfertile strain Y, such as ARP 61, or such as a tetrasporous hybrid strain from ARP 61, such a strain making it possible to have a large number of homocaryons easily available. In this way, a hybrid strain XY is obtained, of which some fructifications will be tetrasporous and from which it will be possible to obtain a large number of homocaryons since the vast majority of the spores formed by the fructifications of such a strain XY are homocaryotic. In the hybrid strain XY and in the spores and the homocaryons derived therefrom, half of the genome originates from strain X. By means of a series of backcrosses with X, an increasing proportion of the genome of X can be incorporated into the hybrids obtained. Owing to the tetrasporous hybrids obtained in each backcross, a large number of homocaryons can finally be obtained in which at least one important trait of a bisporous known strain X has been incorporated.

Owing to the invention, it is even possible to easily obtain, from a bisporous strain X of *Agaricus bisporus*, isogenic tetrasporous strains in the amount desired (for example more than 90% or more than 95%). Large quantities of homocaryons of which most of the genome can be derived from any source of *Agaricus bisporus* (usually bisporous) which is considered attractive, including any existing commercial strain, are therefore available in particular.

In particular, two intercompatible homocaryotic mycelia X1 and X2 can be isolated and identified, which are obtained from a bisporous strain X of *Agaricus bisporus*, for example by the protoplast method. One of the two homocaryons, for example X1, is confronted with a homocaryon of an interfertile tetrasporous strain Y, for example as defined above. A hybrid strain XY is obtained, the fructifications of which provide a high percentage of tetrasporous and/or trisporous basidia. Homocaryons of XY, of which half of the genome originates from strain X, can therefore be obtained easily. Hybrids, in particular tetrasporous hybrids, of which increasing amounts of the genome originate from X, or, more precisely, from X1, can be obtained successively by a series of backcrosses with strain X, using in each case the homocaryon X1 as crossing partner, the tetrasporous hybrids being selected at each stage. In theory, as is easy to determine, these proportions are of the order of 75%, 87.5%, 93.75% and 96.9% after 1, 2, 3 or 4 backcrosses, respectively.

When the desired level of isogeny is obtained, it is even possible to confront a homocaryon of the last tetrasporous hybrid, which has been obtained from backcrosses, with the homocaryon X2, which is known to be compatible with X1. In this manner, hybrids X' are obtained, of which a sizeable proportion of the genome originates from X and which moreover, owing to the last cross with X2, have the heterozygosis which is characteristic of X.

It will be possible for a tetrasporous isogenic hybrid X' to be used as the source for a large number of homocaryons which allow the strain X to be crossed with other attractive strains Z, in particular with the aid of homocaryons of strains Z' which have been made tetrasporous and at least partially isogenic with Z. by the method which has just been set out. Strain Z is, for example, a strain from a site at a distance from the site from which strain X (or the parents of X) originate. A large number of crossing trials of X' and Z or Z' can thus be carried out, in particular with the aim of taking advantage of the vigour which is generally characteristic of hybrids between genetically distant parents.

One of the advantages obtained owing to the fact that the homocaryons become readily available in large quantities is that work can be carried out on a large number of randomly selected homocaryons without there being the risk of a counterselection which is inherent in the small number of homocaryons obtained by traditional routes. However, when the various backcrosses lead to tetrasporous strains which are at least partially isogenic with X (or Z), it is additionally possible to select from amongst the homocaryons those whose performance when crossed with the final hybridization partner (Z in the case of X) are on average satisfactory or may even be highly attractive.

Owing to the invention it is also made easy to introduce an attractive recessive trait of a bisporous strain into another strain. In fact, let for example a be an attractive recessive monogenic trait which is present in a bisporous strain Xaa(b) which is homozygous for the recessive allele a. The symbol (b) designates in this case the bisporous phenotype. It is desired to transfer a into a bisporous strain ZAA(b) which is homozygous for the dominant allele A. To this end, the following procedure may be followed. First, a hybrid XYAa (T) between a homocaryon a(b) of X, which has been obtained by a traditional route (selection of mycelia from spores or protoplasts) and a homocaryon A(T) obtained from germinating a spore of a tetrasporous strain YAA(T) is produced. The symbol (T) designates in this case the dominant tetrasporous phenotype. This hybrid XYAa(T) is tetrasporous, and its spores produce a large number of homocaryons of which some have the type a(T), that is to say carry the allele a and, at the same time, the trait of being tetrasporous. These homocaryons a(T) can be identified since they are the only ones which, when back-crossed with homocaryon a(b) of X, give hybrids which are tetrasporous and, at the same time, show the desired trait a. In a second step, the allele a, which is carried by one of the homocaryons a(T), is introduced into strain ZAA(b) by backcrosses. To this end, two intercompatible homocaryons Z1A(b) and Z2A(b) can be obtained first, for example by the protoplast method. By crossing Z1A(b) with a homocaryon a(T) obtained from XYAa(T), a tetrasporous hybrid can be obtained, and homocaryons which are a(T), that is to say carry the allele a and the trait of being tetrasporous, can again be identified, as shown above, amongst the homocaryons from the spores of this hybrid. These new homocaryons a(T) are backcrossed several times in succession with Z1A (T) until a homocaryon Z'1A(T) which is to a high degree isogenic with Z1A(b), but has the allele a and the trait of being tetrasporous, is obtained.

Crosses of the same type are carried out in parallel starting with Z2A(b) and a homocaryon a(T) obtained from XYAa (T) to arrive at a homocaryon Z'2A(T) which is to a high degree isogenic with Z2A(b).

Finally, the two homocaryons Z'1A(T) and Z'2A(T) are crossed to obtain a heterocaryon Z'aa(T) which is to a high degree isogenic with Z (in particular the heterozygosis in Z is found again in Z'), but is tetrasporous and has the desired character. If desired, the two homocaryons Z'1 and Z'2 which are obtained from each series of backcrosses can also be selected on the basis that they carry the trait of being bisporous. In this case, the final hybrid Z'aa(b) is bisporous.

Of course, the method which has just been described can, with the necessary adaptions being made, be applied to other cases, including when the trait studied is governed by two to three genes at independent loci.

When the trait studied, or the trait which it is desired to incorporate into a hybrid strain, is governed by a sizable number of genes, for example a number of 3 or more, it is generally easier to carry out a bulk selection. In such a case, it will also be easily possible to take advantage of the present invention by following a procedure for example as described hereinbelow.

On a suitable substrate, a primary mycelium obtained from a homocaryon of an attractive mother strain X is multiplied, and said substrate having this primary mycelium is seeded with a plurality of mostly homocaryotic spores or mycelia which have been obtained from a fungus Y which is mostly tetrasporous and/or trisporous and interfertile with *Agaricus bisporus,* Y being, for example, as defined above. The secondary mycelia obtained are then grown under conditions which allow fructification, and carpophores capable of showing the desired trait are selected.

If appropriate, the above-described selection methods can be combined with each other.

Owing to the invention, it is also possible to study the determinism of a given phenotypic trait according to traditional methods which could not be used previously: for example hybridization by means of crossing two parent strains, giving a first generation of hybrids termed F1, followed either by backcrossing with one of the parent strains, or by obtaining a generation of hybrids (termed F2) obtained by crossing between homocaryons obtained from a hybrid F1, and finally studying the hybrids thus obtained.

Moreover, owing to the invention, which allows tetrasporous hybrids to be obtained which give a large number of homocaryons, it is possible to subject the homocaryotic spores which are obtained in large numbers to mutagenesis procedures by known methods. In this case, all the mycelium obtained from mutated monocaryotic spores is mutant.

If homocaryotic fructifications can be obtained (which seems to be possible in the case of *Agaricus bisporus*), the mutant trait can then be observed in the carpophores, even if it is recessive.

The present invention relates to novel Agaricus hybrid strains, that is to say strains obtained by a cross or crosses, which are interfertile with *Agaricus bisporus,* and whose fructifications are characterized in that a small proportion of their basidia are bisporous. In general, the other basidia (which are not bisporous) are tetrasporous and/or trisporous. It is accepted that the spores from bisporous basidia are most frequently homocaryotic, that two thirds of the spores from trisporous basidia are homocaryotic, and that all of the spores from tetrasporous basidia are homocaryotic. The hybrid strains of the invention which have been obtained in the first generation (by crossing with a strain such as ARP 61) are mostly tetrasporous, the proportion of bisporous basidia being below 8% and most frequently below 2%. In the case of hybrids obtained from later crosses, a "tetrasporous type" in which less than 15% (in general less than 7%) of the basidia are bisporous while the other basidia are essentially tetrasporous and trisporous, and a "bisporous type" in which more than 25% of the basidia (in general more than 45%) are bisporous and less than 15% (in general less than 7%) are tetrasporous, can be found. Of course, such strains of the bisporous type are not part of the invention.

One of the remarkable traits of the hybrid strains of the invention which are to a minor extent bisporous (less than 15% bisporous basidia) is thus that most of the spores are homocaryotic. It is easy to calculate that, for example, a strain containing 15% of bisporous basidia, 40% of tetrasporous basidia and 45% of trisporous basidia will give, in principle, more than 75% of homocaryotic spores.

The invention therefore relates to novel hybrid strains of Agaricus having the following traits:

they are interfertile with *Agaricus bisporus,* their fructifications have basidia of which less than 15% are bisporous, and most of the spores are homocaryotic, said traits being genetically transmitted.

In particular, the invention relates to hybrid strains as defined above, whose fructifications have basidia of which at least 40% are tetrasporous. In general, the other basidia (that is to say basidia other than bisporous and tetrasporous ones) have at least three spores and are most frequently tetrasporous. Of course, rare erratic monosporous basidia are ignored in this context.

The invention especially relates to the strains as defined hereinabove in which less than 8% of the basidia are bisporous, as well as strains in which more than 45%, especially more than 50%, of the basidia are tetrasporous.

Of course, the invention embraces all homocaryotic or heterocaryotic forms of these novel hybrid strains, especially carpophores, spores, homocaryons and homocaryotic mycelia obtained in particular by germination of said spores or obtained from protoplasts.

The invention especially embraces those novel hybrid strains which have at least one attractive phenotypic and/or genotypic trait.

The attractive phenotypic traits which are incorporated into the hybrid strain can be especially those which are usually desired in selection procedures in the field of cultivated mushrooms and, in particular, selected from amongs one or more of the following traits: shape, size and colour (in particular white colour) of the carpophores, yield, ability to form fruiting bodies under given conditions and/or on a given substrate, resistance to certain diseases (viral, bacterial or fungal diseases) or to certain treatment products, fruit formation in more or less pronounced clusters, even absent clusters, absence of boulders, type of anchorage (for example firmness of anchorage) and/or organoleptic, nutritional or toxicological traits (for example low level of agaritine and/or derivatives thereof).

The attractive genotypic traits which are imparted to the hybrid strain are, for example, those which result from incorporation of part, or a sizable proportion, of the genomee of a known strain selected for its particular qualities or selected for its particular origin (in particular, in this last case, to exploit the vigour of the hybrids thus obtained, as already indicated above).

The hybrid strains of the invention can therefore be characterized in that they have incorporated such phenotypic and/or genotypic traits.

The invention especially relates to a hybrid strain as defined above which has at least one phenotypic and/or genotypic trait which is not present in the wild-type strains of Agaricus, and basidia which are mostly tetrasporous and interfertile with *Agaricus bisporus*.

The hybrid strains according to the invention are especially those with at least one attractive phenotypic and/or genotypic trait present in a bisporous parent strain or in a parent strain obtained from a bisporous strain.

The invention also relates to a method of obtaining such a hybrid strain in which the majority of spores are capable of producing homocaryons, this method comprising at least one step in which a first homocaryon obtained from a strain of *Agaricus bisporus* is crossed with a second intercompatible homocaryon, characterized:

in that said first homocaryon is selected from amongst those obtained from a strain of *Agaricus bisporus* which has an attractive phenotypic and/or genotypic trait, in that said second homocaryon is selected from amongst those obtained from a strain of Agaricus which is inter-fertile with *Agaricus bisporus* and of which the fructifications have basidia whose spores are mostly homocaryotic, in that said method comprises a step in which hybride strains which have been produced by said cross H and Z2 and which have fructifications with less than 15% of bisporous basidia are selected, and in that, if desired, the spores of said fructifications are collected and/or the homocaryons obtained from said spores are isolated.

In specific embodiments, the method of the invention can also have the following features, either singly or, if appropriate, in combination:

in said selection step, the products of crossing (that is to say the hybrid strains obtained) which have said attractive phenotypic or genotypic trait are also selected (either before or after selection of the hybrid strains whose fructifications have mostly homocaryotic spores) In particular, the products of crossing whose traits are those which have been defined above for the hybrid strains of the invention can be selected;

said strain of *Agaricus bisporus* from which said first homocaryon is obtained is bisporous;

said second homocaryon is obtained from a wild-type strain of Agaricus or else said second homocaryon is derived from a hybrid strain obtained from at least one cross between a bisporous strain of *Agaricus bisporus* and an interfertile strain of Agaricus whose fructifications have spores which are mostly homocaryotic;

additionally, the hybrid strain obtained is backcrossed at least once with a parent strain, that is to say with one of the strains from which said first homocaryon has been obtained, or, if appropriate, said second homocaryon; in particular, said hybrid strain can be backcrossed successively a sufficient number of times so as to incorporate at least a predetermined proportion of the genome of said parent strain and/or to introduce at least one phenotypic trait of said parent strain into the final hybrid; moreover, hybrid strains whose fructifications have basidia of which less than 15% are bisporous can be selected advantageously after each of the successive back-crosses for the following crosses; in a particular embodiment, two homocaryons X1 and X2 which are inter-compatible (derived, for example, from protoplasts) and which are obtained from said parent strain are isolated, and at least one cross is made with X1 and at least one cross is made with X2; for example, a plurality of successive backcrosses is made with homo-caryon X1, with the exception of the last cross which is made with homocaryon X2;

said parent strain being a strain X which has a recessive phenotype with regard to a given trait, one cross is made between said strain X and said second homocaryon, and a homocaryon H is isolated from the hybrids obtained from this cross which has an allele of said recessive trait; moreover, if appropriate, said homocaryon H is confronted with a homocaryon of a second bisporous strain Z of *Agaricus bisporus* which has a dominant phenotype with regard to said trait and, if desired, one or more backcrosses are made with said strain Z, isolating, at each stage, homocaryons having the recessive allele; in a particular embodiment, two intercompatible homocaryons Z1 and Z2 are isolated from Z, they are confronted as above, and this is followed, if appropriate, by backcrosses, on the one hand between H and Z1 in a first series of steps, and, on the other hand, between H and Z2 in a second series of steps, and homocaryons, having the recessive allele, of hybrids obtained from the first and the second series of steps respectively, are backcrossed with each other; of course preferably those homocaryons are isolated after each intermediate step of a cross or backcross which not only have the recessive allele but also which originate from hybrids obtained in this step, of which the fructifications have less than 15% bisporous basidia.

However, the final hybrid will be selected on the basis of bisporous fructifications if it is not desired to follow the selection programme.

The invention also relates to hybrid strains (or spores or homocaryons) which can be obtained in particular according to one of the methods mentioned hereinabove; and to their products of crossing.

The invention also relates to the use of a hybrid strain as defined above as starting material for obtaining modified strains of *Agaricus bisporus,* whether they are bisporous or not.

This use can be accomplished, for example, by one or more of the following methods:

at least one cross is made, with the aid of homocaryons, between said hybrid strain and a strain of Agaricus

*bisporus*, and the products of crossing obtained which have a phenotypic or genotypic trait of said strain of *Agaricus bisporus* are selected;

or a primary mycelium obtained from a homocaryon of a strain of *Agaricus bisporus* is multiplied on a suitable substrate, and said substrate having this primary mycelium is seeded with a plurality of spores or mycelia obtained from a hybrid strain according to the invention;

or the homocaryotic spores of a hybrid strain according to the invention are subjected to mutagenesis procedures;

or at least one gene or gene fragment is inserted into the genome of a homocaryon, a heterocaryon or a protoplast obtained from a hybrid strain according to the invention.

The examples which follow illustrate the invention.

EXAMPLE 1

Strain ARP 61 was used as the parent strain.

This strain is brown. About 90% of the basidia found on the specimens obtained in culture have four spores or more, and about 2% are bisporous.

Its electrophoretic profile in alcohol dehydrogenase (ADH) corresponds to allele 149 (according to D. J. Royse and May, Agric. Biol. Chem. 53(11), 2861–2866, 1989).

This allele 149 is also present in commercial strains such as Somycel 611 (Somycel) or Royal 5A (Royal Champignon).

Its esterase profile shows an allele which can also be found in Canadian strain Ag 89 (ref.: Agaricus Genetics Research Collection, Erindale College, University of Toronto (Canada); this strain having been described by D. Mallock, Mycologia 79(6) pages 839–846, 1987), and in commercial strains such as C45 (Le Lion).

274 single-spore cultures were obtained from spores of ARP 61. Intra-strain confrontations enabled it to be demonstrated that more than 90% of these single-spore cultures are homocaryons and that the strain is bipolar.

Inter-strain confrontations between, on the one hand, tetrasporous strain ARP 61 and, on the other hand, American or French wild-type strains of *Agaricus bisporus*, or commercial strains, gave the following results:

the homocaryons obtained from strain ARP 61 are intercompatible with all homocaryons with which they were contronted and which were derived from a variety of French wild-type strains of *Agaricus bisporus*, from the American wild-type strain Wc 240 (Pennsylvania State University Mushroom Culture Collection, this strain having been described by May and Royse, Mushroom Science, No. X1, pages 799–817, Australia 1981), and from the commercial strains U1 (Somycel), XI(Le Lion), 30A (Royal Champignon), 191 (Somycel).

In all cases, the hybrid strains which have a heterozygotic ADH profile were isolated even though all the homocaryons used for the crosses have a single-band profile.

This confirms the heterocaryotic nature of the hybrids.

The hybrid strains were grown, and most of them formed fruiting bodies.

In all the cases which were studied, with one exception, all the hybrid carpophores have more than 50% (in general between 65 and 85%) of basidia with four spores or more, and less than 8% of basidia with two spores. Germination of cultured spores is normal. This therefore demonstrated the interfertility of the tetrasporous strain ARP 61 and the conventionally bisporous strains.

Strain ARP 61 can be considered as belonging to the species Agaricus bisporus. The trait of being tetrasporous is in addition dominant over the trait of being bisporous.

EXAMPLE 2

Crosses between homocaryons of ARP 61 and homocaryons derived from a protoplast of the commercial strain U1, which produces white fructifications, were made. From the 43 hybrids which were studied from those obtained in the first generation, all are tetrasporous (less than 7%, and in general less than 2%, of bisporous basidia and more than 50%, in general more than 60%, of tetrasporous basidia), with the exception of one hybrid which was more of the bisporous type, this exception being due to accidental contamination. The homocaryons from the spores of one of the hybrids obtained were crossed with a second homocaryon derived from a protoplast of U1 which is intercompatible with the first homocaryon of U1. The genome of the hybrids obtained after this backcross thus originates to the extent of 75% from the genome of U1 and to the extent of 25% from the genome of ARP 61.

As regards the number of spores, from amongst the, 39 hybrids obtained from backcrosses which were studied, 22 are of the bisporous type (more than 25%, in general more than 45%, of bisporous basidia and less than 15%, in general less than 7%, of tetrasporous basidia), and 17 are of the tetrasporous type (less than 15% and in general less than 7% of bisporous basidia, and more than 40%, in general more than 45%, of tetrasporous basidia).

From amongst the 39 hybrids which were studied (21 with white fructifications and 18 with brown fructifications), more than a quarter give fructifications which are white as well as of the tetrasporous type.

It has been noted that the trait of being tetrasporous is generally transmitted together with the sexual trait, which is expressed by the fact that the homocaryons, obtained from the hybrid, which have said trait are generally compatible with the parent homocaryon which does not have this trait. A simple compatibility test thus allows homocaryons obtained from spores of the hybrid to be selected which are capable of transmitting the trait of being tetrasporous (or, more generally, the trait "having fructifications whose spores are mostly homocaryotic").

What is claimed is:

1. A process for producing a tetrasporous heterokaryotic mycelium that is isogenic with a first bisporous strain of *Agaricus bisporus* for at least 50% of its nuclear genome by crossing the first strain with a second wild-type strain that is interfertile with *Agaricus bisporus*, the second strain having fructifications that carry basidia having predominantly homokaryotic spores, to form a heterokaryotic hybrid of the first and second strains, the hybrid having fructifications that carry basidia having predominantly homokaryotic spores, wherein the process comprises:

obtaining first homokaryons of the first strain and second homokaryons of the first strain by isolating protoplasts of the first strain, wherein the first and second homokaryons are intercompatible;

crossing the first homokaryons of the first strain with homokaryons of the second strain, to obtain a first hybrid having a majority of homokaryotic spores;

subjecting homokaryons of the first hybrid to a series of backcrosses with the first homokaryons of the first strain and selecting tetrasporous hybrids at each backcross to obtain a second hybrid having a desired proportion of the genome of the first strain;

crossing homokaryons of the second hybrid with the second homokaryons of the first strain to obtain a third hybrid, the third hybrid having the desired proportion of the genome of the first strain and a nuclear and chromosomal distribution of alleles of the first strain; and culturing the third hybrid to produce the heterokaryotic mycelium.

2. A process for producing a tetrasporous heterokaryotic mycelium that is isogenic with a first bisporous strain of *Agaricus bisporus* for at least 50% of its nuclear genome, the mycelium being homozygous for at least one allele for a recessive character not naturally present in the first strain, wherein the process comprises:

crossing a second strain of *Agaricus bisporus* and a third strain of Agaricus to form a first hybrid, the second strain being homozygous for the at least one allele, the third strain being interfertile with *Agaricus bisporus*, not having the recessive character and having fructifications that carry basidia having predominantly homokaryotic spores, and the first hybrids having fructifications that carry basidia having predominantly homokaryotic spores;

selecting first homokaryons of the first hybrid, the first hybrid being homozygous for the at least one allele and being tetrasporous;

obtaining first homokaryons of the first strain and second homokaryons of the first strain by isolating protoplasts of the first strain, wherein the first and second homokaryons of the first strain are intercompatible;

crossing the first homokaryons of the first hybrid and the first homokaryons of the first strain to obtain a second hybrid;

subjecting homokaryons of the second hybrid to at least one backcross with the first homokaryons of the first strain, selecting homokaryons of a hybrid having fructifications that carry basidia having predominantly homokaryotic spores at each backcross, to obtain a third hybrid being homozygous for the at least one allele and being tetrasporous;

crossing the first homokaryons of the first hybrid and the second homokaryons of the first strain to obtain a fourth hybrid;

subjecting homokaryons of the fourth hybrid to at least one backcross with the second homokaryons of the first strain, selecting homokaryons of a hybrid having fructifications that carry basidia having predominantly homokaryotic spores at each backcross, to obtain a fifth hybrid being homozygous for the at least one allele and being tetrasporous;

crossing homokaryons of the third hybrid and homokaryons of the fifth hybrid to obtain a heterokaryon being homozygous for the at least one allele and having a nuclear and chromosomal distribution of alleles of the first strain; and culturing said heterokaryon to produce the heterokaryotic mycelium.

3. The process of claim 2, wherein said heterokaryon is tetrasporous.

4. The process of claim 2, wherein said heterokaryon is bisporous.

* * * * *